(12) United States Patent
Ikegami et al.

(10) Patent No.: US 11,105,719 B2
(45) Date of Patent: Aug. 31, 2021

(54) SAMPLE PREPROCESSING DEVICE AND ANALYSIS SYSTEM

(71) Applicant: HORIBA, LTD., Kyoto (JP)

(72) Inventors: Kohei Ikegami, Kyoto (JP); Yasushi Hirata, Kyoto (JP); Akihiro Hirano, Kyoto (JP)

(73) Assignee: HORIBA, LTD., Kyoto (JP)

( * ) Notice: Subject to any disclaimer, the term of this patent is extended or adjusted under 35 U.S.C. 154(b) by 96 days.

(21) Appl. No.: 16/555,522

(22) Filed: Aug. 29, 2019

(65) Prior Publication Data

US 2020/0200656 A1 Jun. 25, 2020

(30) Foreign Application Priority Data

Dec. 20, 2018 (JP) .............................. JP2018-238804

(51) Int. Cl.
  *G01N 1/44* (2006.01)
  *G01N 1/42* (2006.01)
  *G01N 33/2025* (2019.01)

(52) U.S. Cl.
  CPC ................. *G01N 1/44* (2013.01); *G01N 1/42* (2013.01); *G01N 33/2025* (2019.01)

(58) Field of Classification Search
  CPC .. G01N 1/34; G01N 1/42; G01N 1/44; G01N 33/2025
  See application file for complete search history.

(56) References Cited

U.S. PATENT DOCUMENTS

| 4,343,199 A * | 8/1982 | Sunna ................... G01N 1/2035 73/863.43 |
| 5,826,983 A * | 10/1998 | Nakamura ............... G01N 5/04 374/14 |
| 2004/0014234 A1* | 1/2004 | Uchihara ........... G01N 33/2025 436/155 |
| 2019/0041335 A1* | 2/2019 | Metz ...................... G01N 21/74 |

FOREIGN PATENT DOCUMENTS

| JP | S53-12393 | 2/1978 |
| JP | S63-265165 A | 11/1988 |
| JP | H11-316220 A | 11/1999 |
| JP | 2009-192233 A | 8/2009 |
| JP | 4560058 B2 | 10/2010 |
| JP | 2017-150847 A | 8/2017 |

OTHER PUBLICATIONS

JPO, Office Action for the corresponding Japanese patent application No. 2018-238804, dated Jul. 15, 2021, with English translation.

* cited by examiner

*Primary Examiner* — Francis C Gray
(74) *Attorney, Agent, or Firm* — Lucas & Mercanti, LLP

(57) ABSTRACT

A sample preprocessing device 2 is to preprocess a sample (W) analyzed by a analysis device 3 by applying heat to the sample, and comprises a heating furnace 4 that applies heat to the sample (W), a discharging port 2P2 from which the sample (W) heated by the heating furnace 4 is discharged by dropping the sample (W), and a posture restriction unit (PR) that restricts a posture of the sample (W) that drops in the discharging port 2P2.

9 Claims, 8 Drawing Sheets

SAMPLE PREPROCESSING DEVICE AND ANALYSIS SYSTEM

CROSS REFERENCE TO RELATED APPLICATION

This Application claims the priority of Japanese Patent Application No. JP 2018-238804 filed on Dec. 20, 2018, application which is incorporated herein by reference.

FIELD OF THE ART

This invention relates to a sample preprocessing device that preprocesses a sample by applying heat to the sample such as, for example, steel, a nonferrous metal or ceramics, and an analysis system using the sample preprocessing device.

BACKGROUND ART

For example, as a method for measuring an oxygen concentration contained in a sample such as steel, a nonferrous metal or ceramics, there is a method wherein a graphite crucible into which a sample is placed is arranged in a heating furnace, the sample is heated and melted while an inactive gas is supplied and carbon monoxide or carbon dioxide that generates at a time when the sample is heated is analyzed by, for example, an infrared gas analyzer.

In order to analyze the oxygen contained in the sample with high accuracy, it is necessary to previously remove oil or dirt (hereinafter called as an adhered substance) that attaches to a surface of the sample or an oxide film. A preprocessing such as heating is conducted in order to remove the adhered substance that attaches to the surface of the sample.

As a contained oxygen analyzer having a function of heating the sample and conducting preprocessing conceived is, as shown in the patent document 1, an analyzer comprising a analysis furnace having a graphite crucible that houses the sample and a preparatory reducing furnace that is arranged on an upper part of the analysis furnace and that conducts preparatory reducing on an oxide film of the surface of the sample by heating the sample at a temperature below the melting point. This analyzer is so arranged that the sample is supplied to the graphite crucible by dropping the sample on which the preprocessing is provided by the preparatory reducing furnace to the inside of the analysis furnace.

However, the analysis device of the above-mentioned arrangement just drops the sample from the preparatory reducing furnace and a posture of the sample while dropping is unstable. Then, there is a case that the sample gets stuck in a communicating path that connects the preparatory reducing furnace and the analysis furnace or an internal path of the analysis furnace before the sample is supplied to the graphite crucible. This problem becomes especially significant in case that the sample is a plate shape or a column shape.

PRIOR ART DOCUMENTS

Patent Document

Patent document 1: Japanese Unexamined Patent Application Publication No. 4560058

SUMMARY OF THE INVENTION

Problems Solved by the Invention

The present claimed invention intends to solve the above-mentioned problem and a main object of this invention is to make it possible to stable supply the sample from the sample preprocessing device to the analysis device.

Means to Solve the Problems

More specifically, a sample preprocessing device in accordance with this invention is a sample preprocessing device that preprocesses a sample by applying heat to the sample to be analyzed by an analysis device, and is characterized by comprising a heating furnace that applies heat to the sample, a discharging port that discharges the sample heated by the heating furnace by dropping the sample, and a posture restriction unit that restricts a posture of the sample that passes the discharging port.

In accordance with this arrangement, since the sample preprocessing device has the posture restriction unit that restricts the posture of the sample while the sample passes the discharging port, the sample is difficult to be stuck in case of supplying the sample from the sample preprocessing device to the analysis device so that it is possible to supply the sample stably.

If the heated sample is supplied to the analysis device as it is, there is a risk that the sample introducing port of the analysis device or its peripheral components might be damaged due to the heat. In order to solve this problem, it is preferable that the sample preprocessing device further comprises a cooling unit that holds and cools the sample heated by the heating furnace. In accordance with this arrangement, it is possible to quickly cool the heated sample on which the preprocessing is conducted and to supply the sample to the analysis device. At this time, if the cooling unit is arranged above the discharging port and functions as the posture restriction unit, it is possible to simplify the structure of the sample preprocessing device.

As a concrete embodiment of the cooling unit, the cooling unit comprises a housing part that houses the sample in a predetermined posture and an open/close mechanism that opens and/or closes an opening part formed on a bottom surface of the housing part. The sample drops while keeping its posture housed in the housing part by opening the opening part of the housing part and dropping the sample by means of the open/close mechanism The cooling unit restricts the posture of the sample that passes the discharging port.

Furthermore, it is preferable that the sample preprocessing device further comprises an introducing port from which the sample is introduced, and a moving mechanism that moves the sample between an inside of the heating furnace and an outside thereof, and the moving mechanism has a sample receiving part that receives the sample from the introducing port, an actuator that moves the sample receiving part and a connecting part that connects the sample receiving part with the actuator. In accordance with this arrangement, if the sample is introduced from the introducing port, the following movement of the sample later can be conducted automatically by the moving mechanism. In addition, since the actuator constitutes the moving mechanism, it is possible to simplify the configuration of the moving mechanism.

In order to simplify the configuration of the moving mechanism, it is preferable that the moving mechanism moves the sample with the posture of the sample kept between the inside of the heating furnace and the outside thereof. In accordance with this arrangement, there is no need of complicated mechanism in order to change the posture of the sample while moving therebetween. Then, for example, if the sample is moved with its posture kept when the sample passes the discharging port, it is possible to simplify the configuration of the sample preprocessing device. If the posture of the sample is kept to be the same as that while passing the discharging port during a process of introducing the sample from the introducing port, it is possible to make the posture of the sample almost constant while the sample moves from the introducing port to the discharging port.

As a concrete embodiment of the heating furnace conceived is the heating furnace that has a heating space horizontally extending from an opening part formed on a side wall of the heating furnace. In this case, it is preferable that the actuator moves the sample receiving part in a horizontal direction and the actuator is arranged on a surrounding side that is orthogonal in the horizontal direction to the heating furnace. With this arrangement, the connecting part has a general channel shape bent or curved between the sample receiving part and the actuator.

An analysis system in accordance with this invention is characterized by comprising the above-mentioned sample preprocessing device and an analysis device that analyzes the sample preprocessed by the sample preprocessing device.

Effect of this Invention

In accordance with the invention having the above-mentioned arrangement, since the sample preprocessing device has the posture restriction unit that restricts the posture of the sample passing the discharging port, it is possible to stably supply the sample from the sample preprocessing device to the analysis device.

MODE FOR EMBODYING THE INVENTION

An analysis system in accordance with one embodiment of this invention will be explained with reference to drawings.
<Device Configuration>
An analysis system 100 of this embodiment is to reduce a sample (W) such as, for example, steel, a nonferrous metal or ceramics by heating the sample (W), and to analyze an element such as O, N, H or the like in the sample (W) contained in a gas produced by the reduced sample (W). The sample (W) of this embodiment forms, for example, a shape of a plate such as a rectangular plate or a shape of a column such as cylinder.

Figure 1:
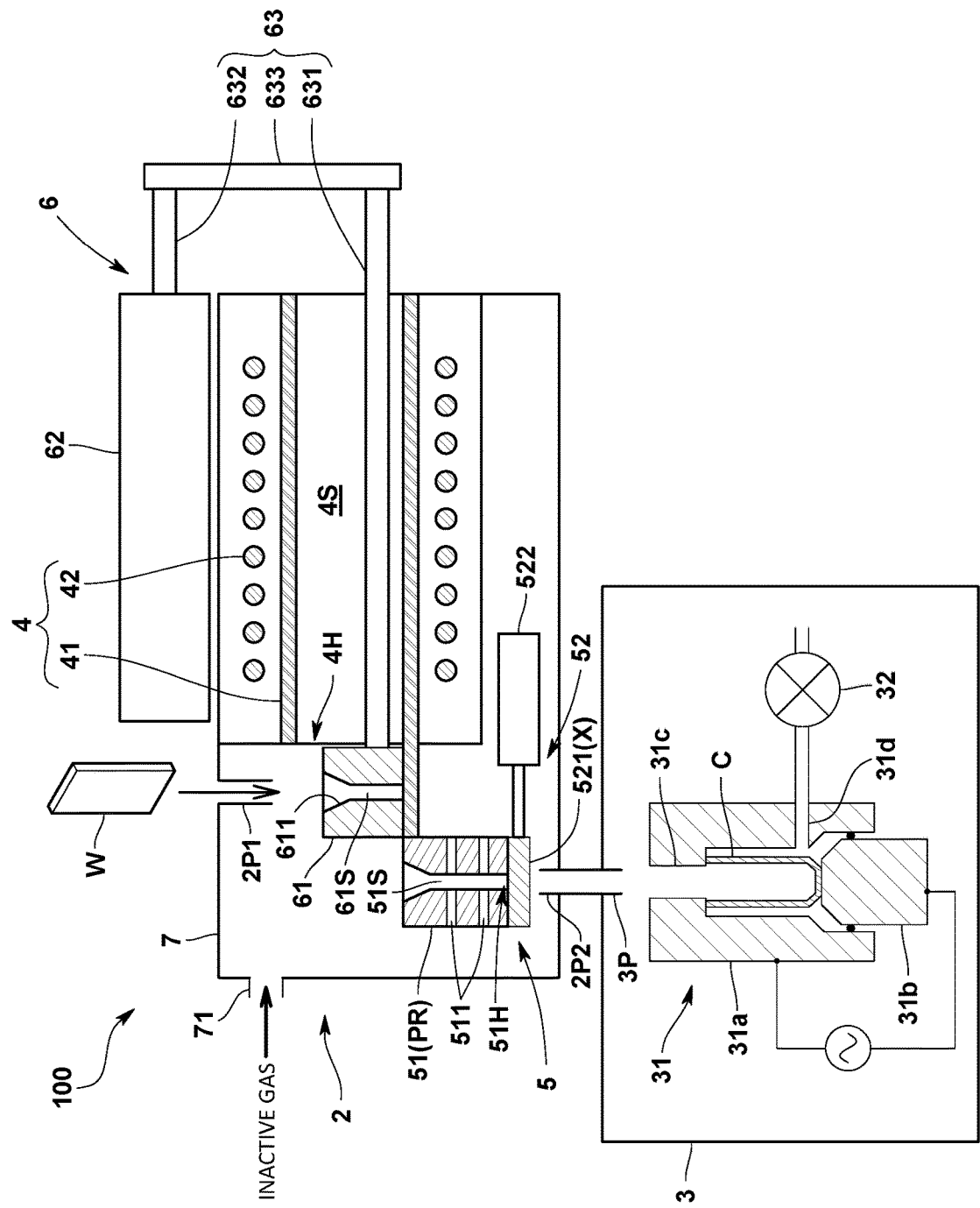
FIG. 1 A diagram schematically showing a configuration of an analysis system of this embodiment.

Concretely, the analysis system 100 comprises, as shown in FIG. 1, a sample preprocessing device 2 that previously removes an adhesive material or an oxide film that attaches to a surface of the specimen (W), and an analysis device 3 that analyzes the sample (W) preprocessed by the sample preprocessing device 2. The sample preprocessing device 2 is arranged above the analysis device 3 and introduces the preprocessed sample (W) from a sample introducing port 3P arranged above the analysis device 3.

First, a configuration of the analysis device 3 will be explained.

The analysis device 3 comprises, as shown in FIG. 1, an analysis furnace 31 where a graphite crucible (C) into which the sample (W) is housed and a gas analyzer 32 that analyzes the gas generated from the combusted sample (W) by being heated in the analysis furnace 31.

The analysis furnace 31 dummy heats the graphite crucible (C) where no sample (W) is housed or heats the graphite crucible (C) where the sample (W) is housed so as to produce the gas by applying heat to the sample (W).

Concretely, the analysis furnace 31 comprises an upper electrode 31$a$ and a lower electrode 31$b$ to electrically heat the graphite crucible (C). The graphite crucible (C) is sandwiched between the upper electrode 31$a$ and the lower electrode 31$b$ and held by them and the graphite crucible (C) is electrically heated by applying voltage to the upper electrode 31$a$ and the lower electrode 31$b$ so that the sample (W) in the graphite crucible (C) is heated. A sample introducing path 31$c$ to introduce the sample (W) and a gas discharging path 31$d$ to discharge the gas produced by the sample (W) into the gas analyzer 32 are formed on the upper electrode 31$a$. The sample introducing path 31$c$ communicates with an upper opening of the graphite crucible (C). In addition, the sample introducing path 31$c$ is connected to the sample introducing port 3P of the analysis device 3 arranged above the analysis furnace 31.

The gas analyzer 32 analyzes the gas generated by the analysis furnace 31 and obtains content of each component contained in the sample (W). In this embodiment, for example, a non-dispersive infrared absorption method (NDIR method) is used to conduct the analysis. Concretely, the gas analyzer 32 has a non-dispersive infrared detector, not shown in drawings, and obtains content of oxygen (O) contained in the sample (W) by detecting $CO_2$, CO or the like contained in the gas discharged from the analysis furnace 31.

Next, the sample preprocessing device 2 will be explained.

The sample preprocessing device 2 comprises, as shown in FIG. 1, an introducing port 2P1 from which the sample (W) is introduced, a heating furnace 4 that applies heat to the sample (W) introduced from the introducing port 2P1, a cooling unit 5 that holds and cools the sample (W) heated by the heating furnace 4, a moving mechanism 6 that moves the sample (W) heated between the inside of the heating furnace 4 and the outside thereof and a discharging port 2P2 from which the sample (W) cooled by the cooling unit 5 is discharged.

The introducing port 2P1 is arranged on a housing 7 that covers an opening part 4H of the heating furnace 4 and the cooling unit 5. An inert gas such as a helium gas or an argon gas is supplied from an inert gas supply unit 71 to the inside of the housing 7 so that the housing 7 is filled with the inert gas.

The heating furnace 4 has a heating space 4S that extends in a horizontal direction from the opening part 4H formed on a side wall of the heating furnace 4 and heats the sample (W) in the heating space 4S, and comprises a furnace body 41 into which the sample (W) is put or from which the sample (W) is removed, an electric resistor 42 that is arranged around the furnace body 41 and that heats the furnace body 41 and a power supply circuit (not shown in drawings) that supplies electric power to the electric resistor 42 and energizes the electric resistor 42 and generates power.

The furnace body 41 is, for example, a tubular ceramic molding, and has a heating space 4S inside of which the sample (W) can be housed. In this embodiment, the furnace body 41 is made of a silica tube. One end part of the furnace body 41 communicates with the opening part 4H. In addition, a connecting part 63 (a first arm part 631) of the moving mechanism 6, to be described later, is inserted into the other end of the furnace body 41. Furthermore, a bottom wall part of the furnace body 41 extends forward in front of the opening part 4H to the cooling unit 5 arranged in front of the heating furnace 4.

The cooling unit 5 is arranged above the discharging port 2P2, and functions as a posture restriction unit (PR) that restricts a posture of the sample (W) passing the discharging port 2P2.

Concretely, the cooling unit 5 comprises a housing part 51 that houses the sample (W) in a predetermined posture, and an open/close mechanism 52 that opens or closes an opening part 51H formed on a bottom surface of the housing part 51.

Figure 2:
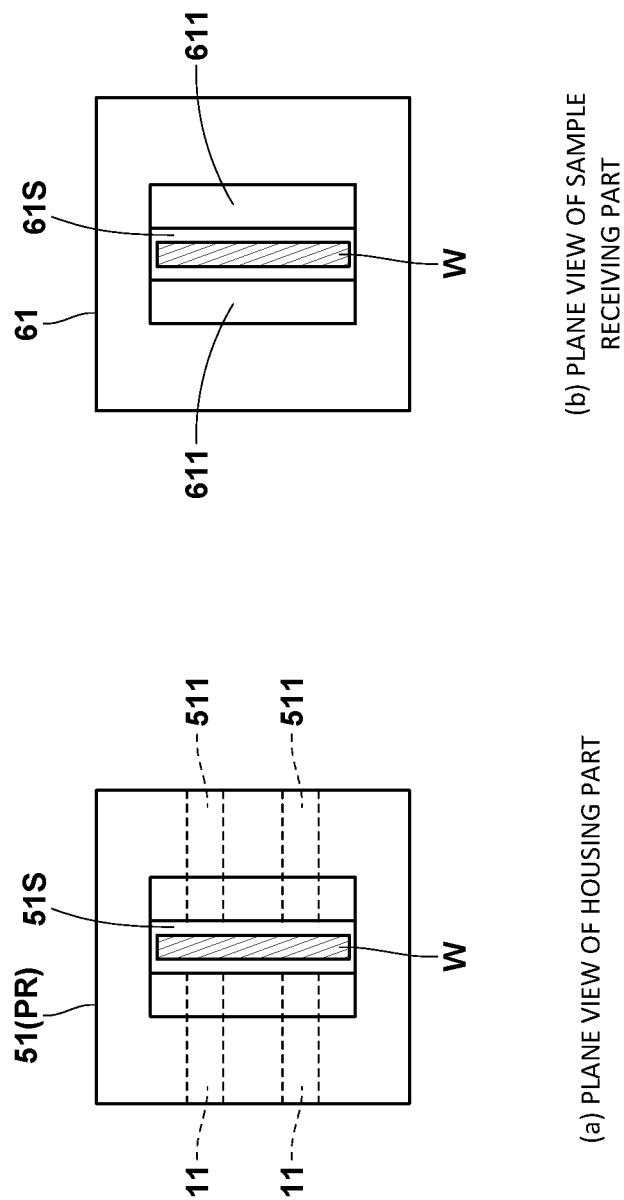
FIG. 2 A plane view of a sample receiving part and a housing part of this embodiment.

The housing part 51 serves as the posture restriction unit (PR). In this embodiment, since the sample (W) is supposed to be a rectangular flat plate shape, the housing part 51 keeps the sample (W) in an upright state with its longitudinal direction facing a vertical direction. The housing space 51S of the housing part 51 is so configured, as shown in FIG. 2(a), a space whose transverse directional cross section is rectangular, and a size of the lateral direction is a little longer than a plate thickness of the sample (W), and a size of the longitudinal direction is a little longer than a width of the sample (W). The housing part 51 is made of, for example, stainless steel.

In addition, one or multiple air vents 511 are formed on a sidewall of the housing part 51 in order make it easy to cool the housed sample (W). It is possible to diffuse the inert gas to the sample (W) without fail by forming the air vent 511 on the housing part 51. As a result of this, since the sample (W) can be exposed to the inert gas atmosphere without fail, it is possible to prevent the sample (W) from being oxidized again.

In addition, the open/close mechanism 52 opens or closes the opening part 51H formed on the bottom surface of the housing part 51, and the opening part 51H has the same cross-section as that of the housing space 51S of the housing part 51 in the transvers directional cross section. With this arrangement, the sample (W) drops without being stuck in the opening part 51H when the opening part 51H is opened by the use of the open/close mechanism 52. The open/close mechanism 52 in this embodiment has a shutter member 521 that closes the opening part 51H and an actuator 522 that moves the shutter member 521. It is conceivable that the actuator 522 has an arrangement using a motor and a ball screw mechanism or an arrangement using a cylinder device. The shutter member 521 moves between a closed position (X) (refer to FIG. 1) where the opening part 51H is closed and an open position (Y) (refer to FIG. 6) where the opening part 51H is opened by means of the actuator 522.

If the open/close mechanism 52 of the cooling unit 5 opens the opening part 51H of the housing part 51, the sample (W) drops downward from the opening part 51H. At this time, the posture of the sample (W) is restricted by an inner surface that forms the housing space 51S of the housing part 51, and the posture of the sample (W) that passes the discharging port 2P2 is restricted.

The discharging port 2P2 may be formed directly under the opening part 51H of the housing part 51, and may utilize the opening part 51h of the housing part 51 as the discharging port 2P2.

The moving mechanism 6 moves the sample (W) introduced from the introducing port 2P1 to the heating furnace 4 and then moves the sample (W) to the cooling unit 5.

Concretely, the moving mechanism 6 has a sample receiving part 61 that receives the sample (W) from the introducing port 2P1, an actuator 62 that moves the sample receiving part 61 and a connecting part 63 that connects the sample receiving part 61 with the actuator 62.

The sample receiving part 61 receives the sample (W) introduced from the introducing port 2P1 and holds the sample (W) when the sample (W) is moved. The sample receiving part 61 has a holding space 61S to hold the sample (W). Similar to the above-mentioned housing part 51, the sample receiving 61 holds the sample (W) in an upright state wherein the longitudinal direction of the sample (W) faces the vertical direction. The holding space 61S is so configured, as shown in FIG. 2(b), a space whose transverse directional cross section is rectangular, and a size of the lateral direction is a little longer than a plate thickness of the sample (W), and a size of the longitudinal direction is a little longer than a width of the sample (W). An inclined guide surface 611 is formed on an upper surface of the sample receiving part 61 and an upper opening of the holding space 61H expands in order to facilitate receiving the sample (W) introduced from the introducing port 2P1.

The sample receiving part 61 of this embodiment is made of graphite, and promotes reduction of the sample (W) in the heating furnace 4 by the sample receiving part 61 itself. In case that the sample receiving part 61 is not made of graphite, it can be conceived that graphite is arranged in the heating furnace 4 to promote reduction or that the sample receiving part 61 is additionally provided with graphite.

Figure 4:
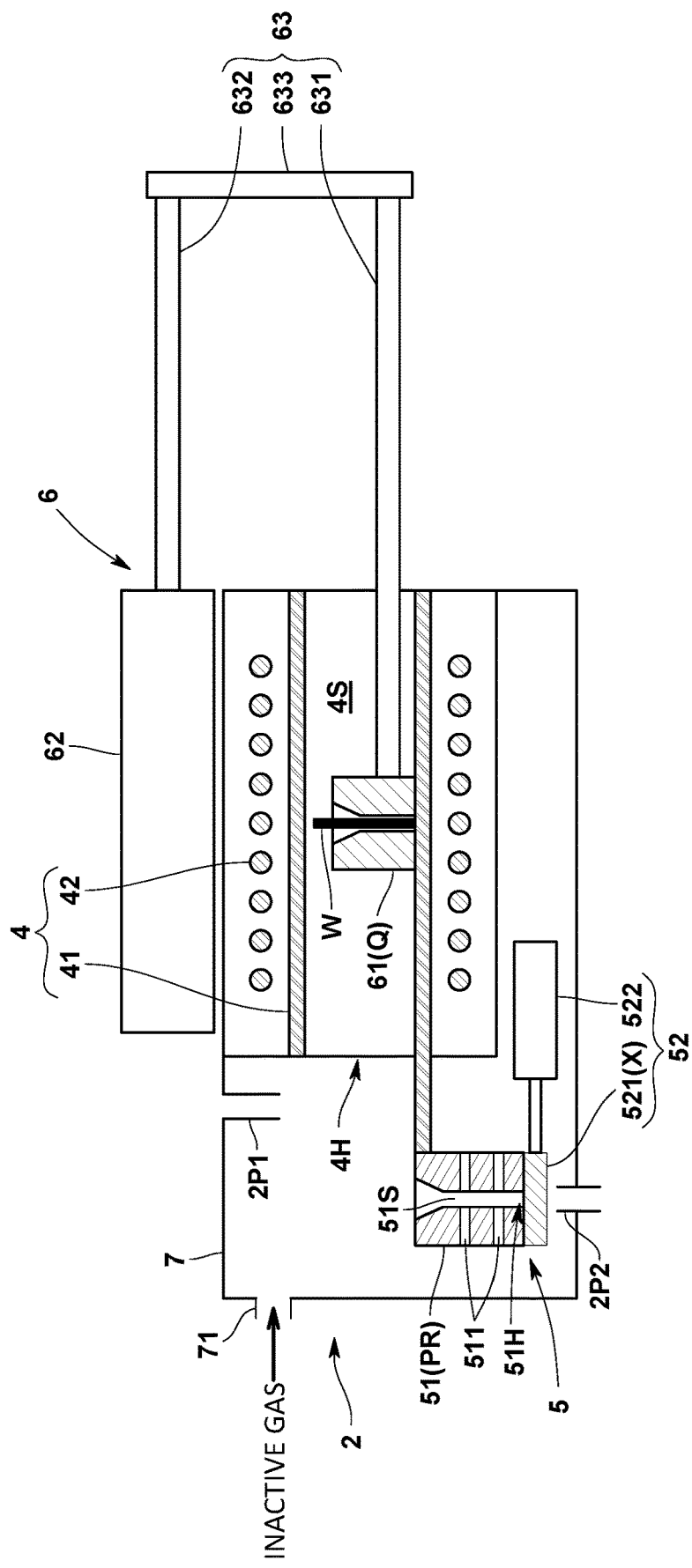
FIG. 4 A diagram showing a heating process of this embodiment.
Figure 5:
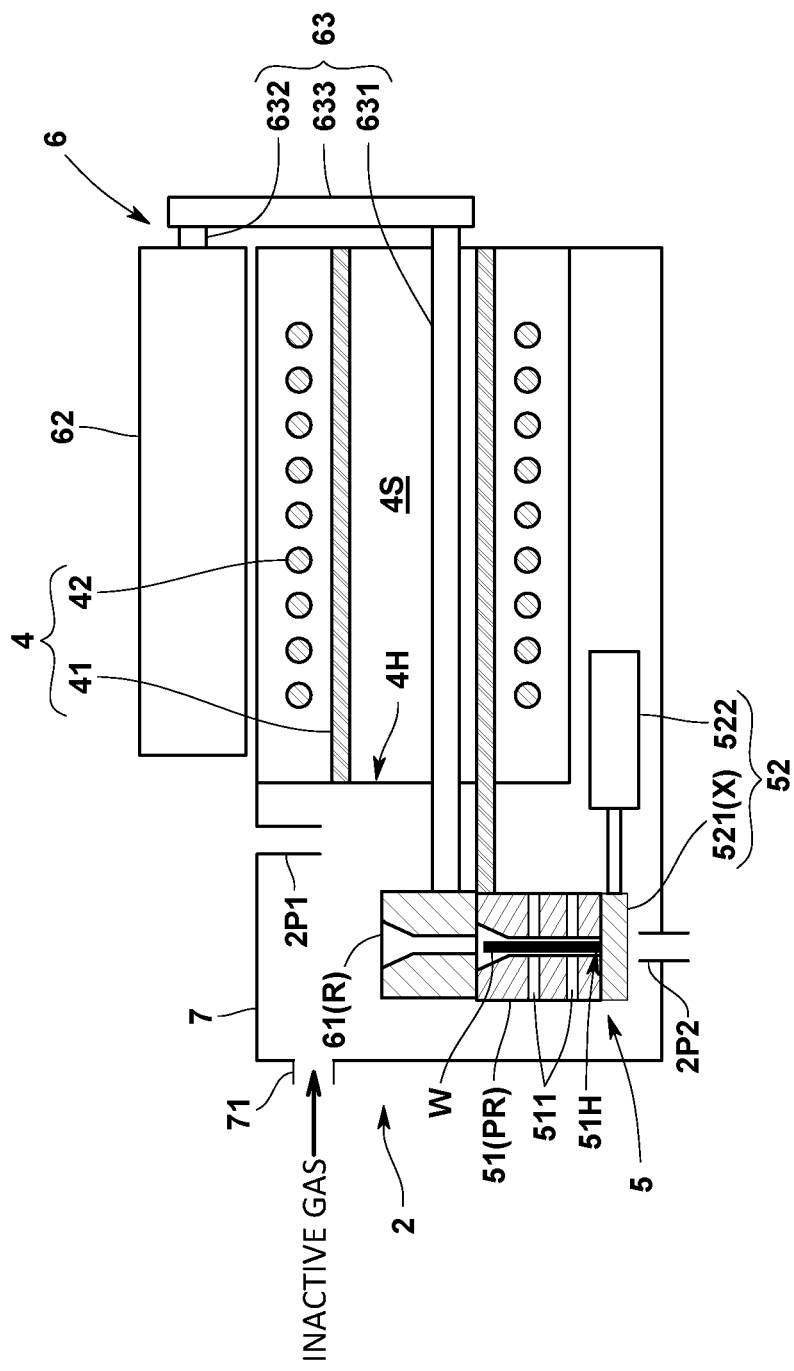
FIG. 5 A diagram showing a cooling process of this embodiment.

The actuator 62 slidingly and linearly moves the sample receiving part 62 among (1) a receiving position (P) where the sample (W) is received from the introducing port 2P1 (refer to FIG. 3), (2) a heating position (Q) set in the heating furnace 4 (refer to FIG. 4) and a delivering position (R) where the sample (W) is delivered to the cooling unit 5 (refer to FIG. 5). It can be conceived that the actuator 62 has an arrangement using a motor or a ball screw mechanism or using a cylinder device.

The actuator 62 is, as shown in FIG. 1, arranged on a surrounding side that is orthogonal to a horizontal direction of the heating furnace 4. The actuator 62 is arranged above the heating furnace 4 in this embodiment, however, the actuator 62 may be arranged under the heating furnace 4 or the actuator 62 and the heating furnace are arranged side-by-side.

The connecting part 63 that connects the sample receiving part 61 and the actuator 62 comprises, as shown in FIG. 1, a first arm part 631 in a side of the sample receiving part 61 that is inserted into the heating furnace 4, a second arm part 632 in a side of the actuator 62 that is not inserted into the heating furnace 4 and a connection arm 633 that connects the first and second arm parts 631, 632. Since the first arm part 631 is inserted into the heating furnace 4, the first arm part 631 is made of a heat resistant member such as, for example, silica. In addition, the sample receiving part 61 is detachably mounted on the first arm part 631 so that it becomes possible to exchange the sample receiving part 61 when it is consumed, and it is possible to exchange it to the sample receiving part 61 suitable for the size or the shape of the sample (W).

Next, an action of the sample preprocessing device 2 will be explained with reference to FIG. 3 through FIG. 6.

Figure 3:
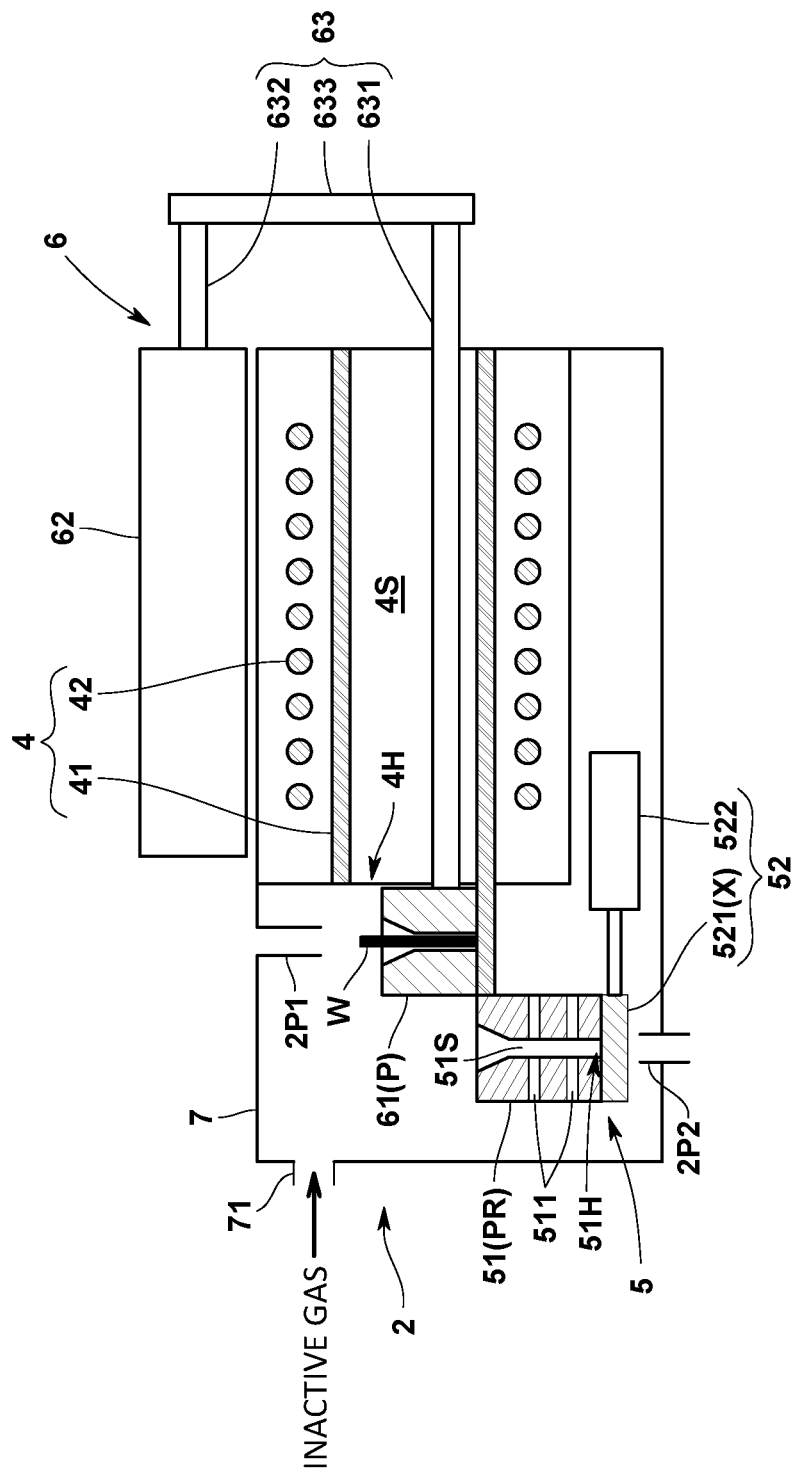
FIG. 3 A diagram showing an introducing process of this embodiment.

(1) Introducing Process (Refer to FIG. 3)

The sample receiving part 61 is moved to the receiving position (P) by controlling the moving mechanism 6 by a control unit, not shown in drawings. With this state kept, the sample (W) is introduced (put) from the introducing port 2P1 by a user or by a transporting hand. In this state, the inactive gas is filled inside of the housing 7.

(2) Heating Process (Refer to FIG. 4)

After the sample receiving part 61 receives the sample (W), the sample receiving part 61 is moved to the heating position (Q) by the moving mechanism 6. With this process, the sample (W) is heated at the heating position (Q), and an adhesive material or an oxide film on the surface of the sample (W) is removed. A heating condition is, for example, 1 minute at 1000° C.

(3) Cooling Process (Refer to FIG. 5)

After the sample (W) is heated, the sample receiving part 61 is moved to the delivering position (R) by the moving mechanism 6. When the sample receiving part 61 is moved to the delivering position (R), the sample receiving part 61 and the housing part 51 of the cooling unit 5 locate on the same vertical straight line. In other words, the holding space of the sample receiving part 61 and the housing space of the housing part 51 are in a vertically communicating state. According to this arrangement, the sample (W) drops from the sample receiving part 61 toward the housing part 51 with its posture kept. As a result of this, the sample (W) is cooled by the cooling unit 5. At this time, cooling of the sample (W) is promoted also by the inactive gas supplied to the inside of the housing 7. In addition, after the sample (W) is delivered, the sample receiving part 61 is moved to the heating position (Q) of the heating furnace 4 and heated until the next introducing process.

Figure 6:
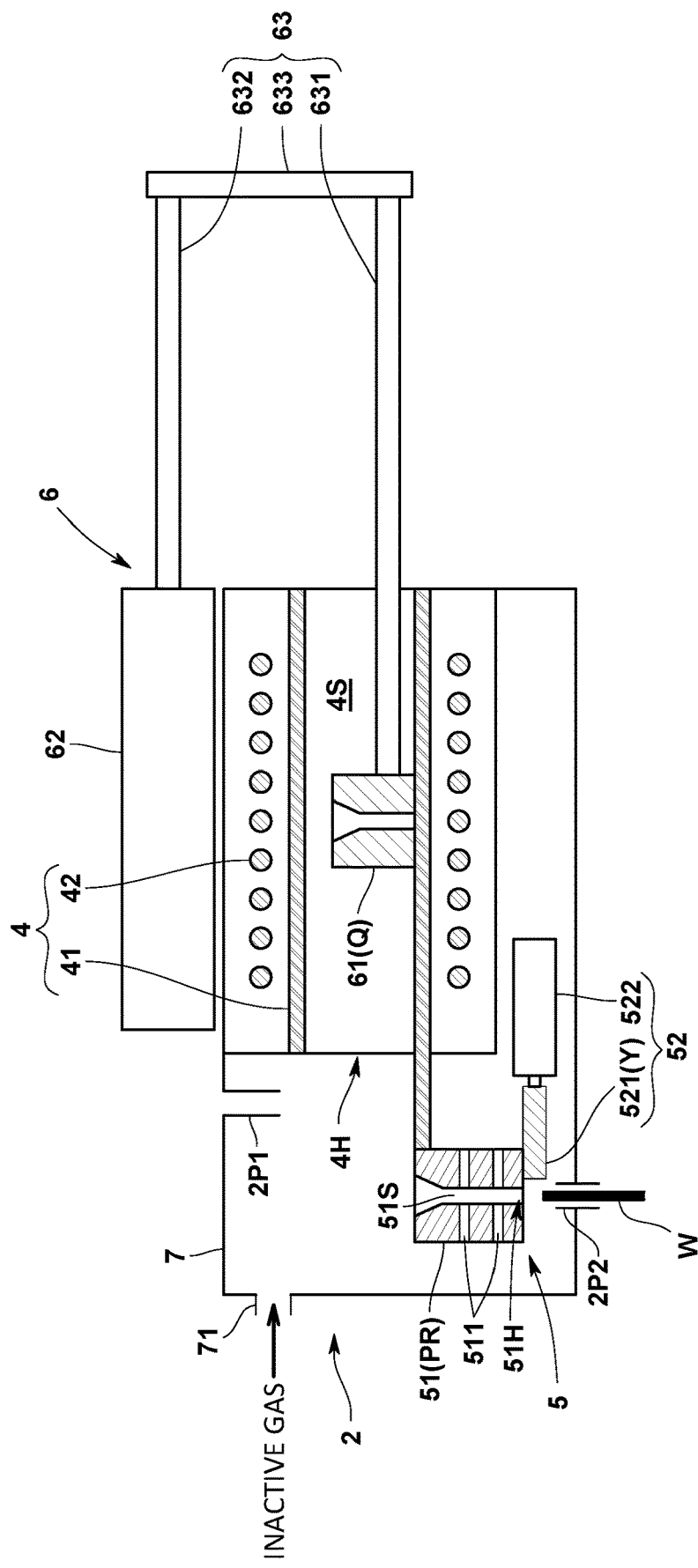
FIG. 6 A diagram showing a discharging process of this embodiment.

(4) Discharging Process (Refer to FIG. 6)

After a predetermined period of time (for example, 1 minute) from initiation of the cooling process, a shutter member 521 of the cooling unit 5 is moved from the closed position (X) to the open position (Y) by controlling the actuator 522 of the cooling unit 5 by the control unit. With this process, the sample (W) drops from the housing part 51 of the cooling unit 5 to the discharging port 2P2 and is introduced into the introducing port 2P1 of the analysis device 3. At this time, since the posture of the sample (W) is restricted by the inner surface that forms the housing space 51S of the housing part 51, the posture of the sample (W) passing the discharging port 2P2 (the sample introducing port 3P of the analysis device 3) is restricted.

Effect of this Embodiment

In accordance with the analysis system 100 of this embodiment, since the analysis system 100 has the posture restriction unit (PR) that restricts the posture of the sample (W) that passes the discharging port 2P2, the sample (W) is difficult to be stuck when the sample (W) is supplied from the sample preprocessing device 2 to the analysis device 3 so that it is possible to stably supply the sample (W).

In addition, since the heated sample (W) is cooled by the cooling unit 5, it is possible to quickly cool and provide the preprocessed sample (W) to the analysis device 3. In accordance with this arrangement, it is possible to prevent the sample introducing port 3P and its peripheral members of the analysis device 3 from being damaged by heat. Since the cooling unit 5 functions as the posture restriction unit (PR), it is possible to simplify the device structure.

Furthermore, since the moving mechanism has the sample receiving part 61 that receives the sample (W) from the introducing port 2P1, the actuator 62 that moves the sample receiving part 61 and the connecting part 63 that connects the sample receiving part 61 with the actuator 62, when the sample (W) is introduced from the introducing port 2P1, the sample (W) can be automatically moved later by the moving mechanism 6. In addition, since the moving mechanism 6 uses the actuator 62, it is possible to simplify the configuration of the moving mechanism.

In addition, since the moving mechanism 6 moves the sample (W) between the inside of the heating furnace 4 and outside thereof with its posture kept, there is no need of complicated mechanism in order to change the posture of the sample (W) while moving therebetween. Then, for example, if the sample (W) is moved with its posture kept when the sample (W) passes the discharging port 2P2, it is possible to simplify the configuration of the sample preprocessing device 2. If the posture of the sample (W) is kept to be the same as that while passing the discharging port 2P2 during a process of introducing the sample (W) from the introducing port 2P1, it is possible to make the posture of the sample (W) almost constant while the sample (W) moves from the introducing port 2P1 to the discharging port 2P2.

In addition, since the actuator 62 arranged above the heating furnace 4, it is possible to make a footprint of the sample preprocessing device 2 small, and furthermore to make the footprint of the analysis system 100 small.

Other Modified Embodiment

The present claimed invention is not limited to the above-mentioned embodiment.

For example, the posture restriction unit (PR) comprises the cooling unit 5 in the above-mentioned embodiment, however, the posture restriction unit (PR) may have an arrangement wherein a pathway is arranged to keep the posture of the sample (W) between the cooling unit 5 and the discharging port 2P2.

In addition, the cooling unit 5 is arranged in front of the heating furnace 4 in the above-mentioned arrangement, however the cooling unit 5 may be omitted. In this case, in case of cooling the heated sample (W), the sample receiving part 61 may be positioned and wait in front of the heating furnace 4 in a state that the sample (W) is held by the sample receiving part 61 for a predetermined period of time. At this time, the sample receiving part 61 functions as the posture restriction unit (PR).

Furthermore, the moving mechanism 6 moves the sample (W) with its posture kept in the above-mentioned embodiment, however, the posture of the sample (W) may be changed while the sample (W) moves. In this case, in case that the sample (W) passes the discharging port 2P2, the posture of the sample (W) is restricted by the posture restriction unit (PR) comprising, for example, the cooling unit 5.

The cooling unit 5 of the above-mentioned embodiment has an arrangement wherein the opening part 51H of the housing part 51 is opened/closed by moving the shutter member 521 with the housing part 51 fixed, however, the opening part 51H may be opened/closed by moving the housing part 51 with the shutter member 521 fixed.

Figure 7:
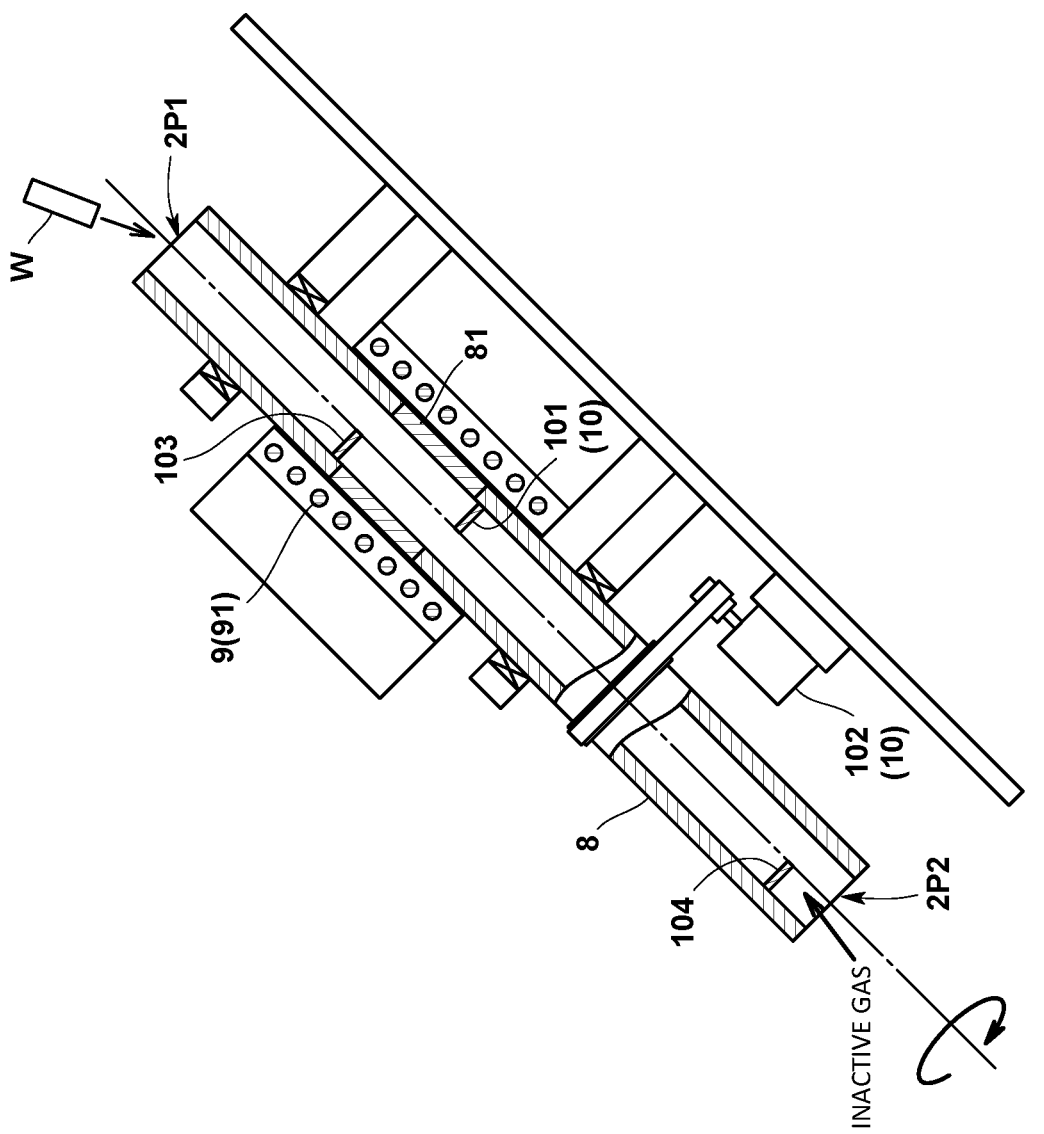
FIG. 7 A schematic diagram showing a configuration of a sample preprocessing unit of a modified embodiment.

In addition, the sample preprocessing device may have an arrangement shown in FIG. 7.

The sample preprocessing device 2 shown in FIG. 7 comprises a sample moving tube 8 that has the introducing port 2P1 and the discharging port 2P2 and where the sample (W) moves due to gravity, a heating mechanism 9 that heats a predetermined portion between the introducing port 2P1 and the discharging port 2P2 of the sample moving tube 8 and a stopper mechanism 10 that halts the sample (W) that moves due to its own weight at the above-mentioned predetermined portion.

The sample moving tube 8 is, for example, a silica tube having a shape of a straight pipe, and is arranged in a tilted state. Then an upper end opening becomes the introducing port 2P1 and a down end opening becomes the discharging port 2P2. In addition, the inactive gas is introduced from the discharging port 2P2 into the introducing port 2P1.

The heating mechanism 9 is arranged to surround the predetermined portion of the sample moving tube 8, and has an electric resistor 91 arranged at the circumference of the sample moving tube 8 and a power circuit (not shown in drawings) that supplies electric power to the electric resistor 91 and energizes and generates heat. With this arrangement, the predetermined portion of the sample moving tube 8 heated by the heating mechanism 9 becomes the heating furnace 4. The predetermined portion of the sample moving tube 8 is provided with graphite. In this embodiment, graphite is arranged at the predetermined portion by constituting a part of the sample moving tube 8 with the graphite tube 81.

The stopper mechanism 10 has a first stopper plate 101 that partitions a part of the sample moving tube 8 to halt the sample (W) at the predetermined portion of the sample moving tube 8 and a rotating part 102 that flips the first stopper plate 101 vertically by rotating the sample moving tube 8. The rotating part 102 rotates the sample moving tube 8 by the use of a motor and a belt.

The first stopper plate 101 is arranged inside of the sample moving tube 8 and partitions the inside of the sample moving tube 8 while securing a space where the sample (W) can pass through. In addition, as shown in FIG. 7, a second stopper plate 103 to make the sample (W) before heated stand by is arranged in the introducing port 2P1 side of the first stopper plate 101, and a third stopper plate 104 to hold the sample (W) in order to cool the sample (W) after heated is arranged in the discharging port 2P2 side of the first stopper plate 101. The second stopper plate 103 and the third stopper plate 104 are arranged at reversing positions to the first stopper plate 101, and partitions the inside of the sample moving tube 8 while securing a space where the sample (W) can pass through. The second stopper plate 103 and the third stopper plate 104 may be omitted.

Figure 8:
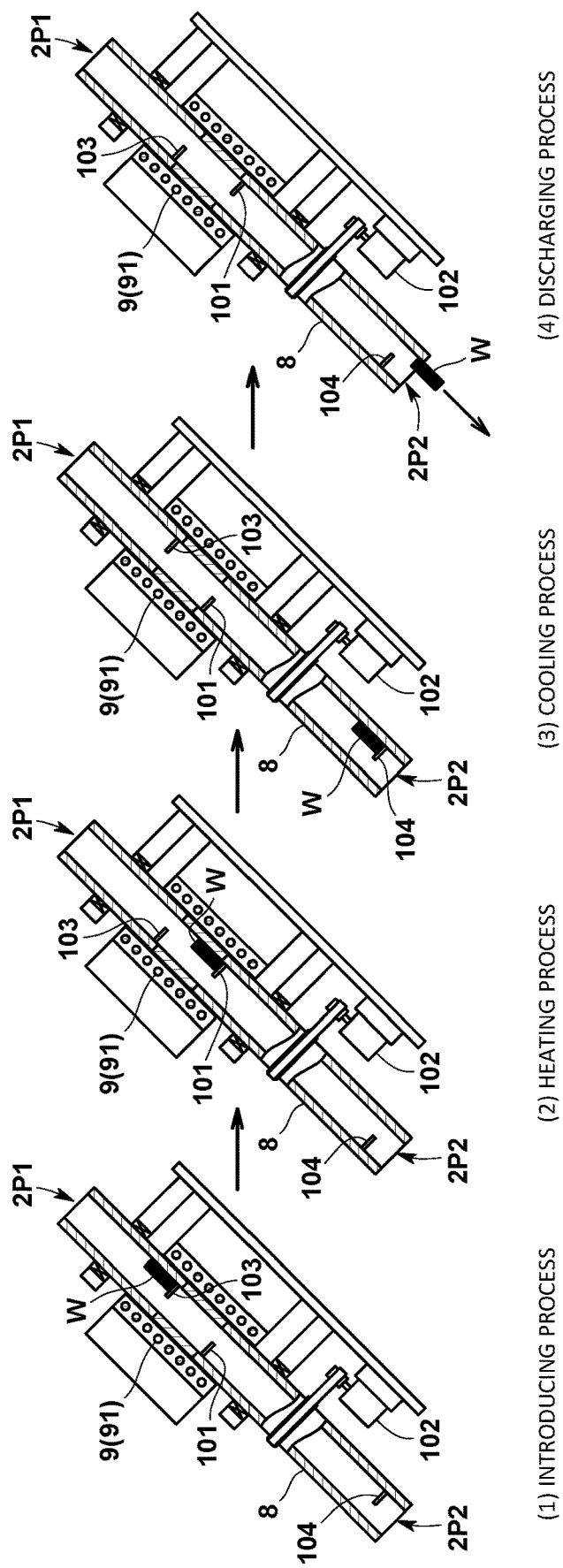
FIG. 8 A schematic diagram showing an operation of the modified embodiment.

Next, an operation of the sample preprocessing device 2 will be explained with reference to FIG. 8.

(1) Introducing Process

The rotating part 102 of the stopper mechanism 10 is controlled to locate the first stopper plate 101 in the upper side and the second stopper plate 103 in the lower side by the control unit, not shown in drawings. In this state, the predetermined portion (the graphite tube 81) of the sample moving tube 8 is heated to a predetermined temperature by the heating mechanism 9. Then the sample (W) is introduced from the introducing port 2P1 of the sample moving tube 8. Then, the sample (W) drops in the sample moving tube 8 by its own weight, reaches the second stopper plate 103 and then resides at this position to be in a stand-by state.

(2) Heating Process

When the sample moving tube 8 is rotated at a predetermined angle (for example 180°) by the rotating part 102 of the stopper mechanism 10 in a state wherein the sample (W) is in the stand-by state by the second stopper plate 103, the second stopper plate 103 locates at the upper side and the first stopper plate 101 locates at the lower side. At this time, halted state of the sample (W) by the second stopper plate 103 is released so that the sample (W) slides down in the sample moving tube 8 by its own weight, reaches the first stopper plate 101 and then resides at this position. The sample (W) is heated in a state wherein the sample (W) is halted by the first stopper plate 101 so that an adhesive material or an oxide film on the surface of the sample (W) is removed.

(3) Cooling Process

After the heating process is finished, when the sample moving tube 8 is rotated at a predetermined angle (for example 180°) by the rotating part 102 of the stopper mechanism 10, the first stopper plate 101 locates at the upper side and the third stopper plate 104 locates at the lower side. At this time, halted state of the sample (W) by the first stopper plate 101 is released so that the sample (W) slides down in the sample moving tube 8 by its own weight, reaches the third stopper plate 104 and then resides at this position. The sample (W) is cooled in a state wherein the sample (W) is halted by the third stopper plate 104.

(4) Discharging Process

After the cooling process is finished, when the sample moving tube 8 is rotated at a predetermined angle (for example 180°) by the rotating part 102 of the stopper mechanism 10, the third stopper plate 104 locates at the upper side. At this time, halted state of the sample (W) by the third stopper plate 104 is released so that the sample (W) slides down in the sample moving tube 8 by its own weight, and then is discharged from the discharging port 2P2.

In accordance with the sample preprocessing device 2, since the preprocessed sample (W) moves while making a sliding movement in the sample moving tube 8, the posture of the sample (W) in case of passing the discharging port 2P2 is restricted by the sample moving tube 8. As this result, the sample (W) is difficult to be stuck when the sample (W) is supplied from the sample preprocessing device 2 to the analysis device 3 so that it is possible to stably supply the sample (W).

In the above-mentioned embodiment, the sample is housed in the graphite crucible and the housed sample is heated and melted, however, other heating method may be applied.

In addition, the present claimed invention may be variously combined or modified without departing from a spirit of the invention.

EXPLANATION OF CODES

100 . . . analysis system
W . . . sample
2 . . . sample preprocessing device
3 . . . analysis device (element analyzer)
2P1 . . . introducing port
2P2 . . . discharging port
4 . . . heating furnace 4H . . . opening part
PR . . . posture restriction unit
5 . . . cooling unit
52 . . . open/close mechanism
6 . . . moving mechanism
61 . . . sample receiving part
62 . . . actuator
63 . . . connecting part

The invention claimed is:

1. A sample preprocessing device that preprocesses a sample by applying heat to the sample to be analyzed by an analysis device, comprising
 a heating furnace that applies heat to the sample,
 a discharging port from which the sample heated by the heating furnace is discharged by dropping the sample, and
 a posture restriction unit that restricts a posture of the sample that passes the discharging port, wherein
 the posture restriction unit comprises a housing part that houses the sample in a predetermined posture and an open/close mechanism that opens and/or closes an opening part formed on a bottom surface of the housing part, and
 the posture restriction unit restricts the posture of the sample that passes the discharging port by opening the opening part of the housing part and dropping the sample by means of the open/close mechanism.

2. The sample preprocessing device described in claim 1, further comprising
 a cooling unit that holds and cools the sample heated by the heating furnace, wherein
 the cooling unit is arranged above the discharging port and functions as the posture restriction unit.

3. The sample preprocessing device described in claim 1, further comprising
 an introducing port from which the sample is introduced, and
 a moving mechanism that moves the sample between an inside of the heating furnace and an outside thereof, wherein
 the moving mechanism has a sample receiving part that receives the sample from the introducing port, an actuator that moves the sample receiving part and a connecting part that connects the sample receiving part with the actuator.

4. The sample preprocessing device described in claim 3, wherein
 the moving mechanism moves the sample with the posture of the sample kept between the inside of the heating furnace and the outside thereof.

5. The sample preprocessing device described in claim 3, wherein
 the heating furnace has a heating space that horizontally extends from an opening part formed on a side wall of the heating furnace, and
 the actuator moves the sample receiving part in a horizontal direction and the actuator is arranged on a surrounding side that is orthogonal to the horizontal direction of the heating furnace.

6. The sample preprocessing device described in claim 3, wherein
 the sample receiving part is made of graphite.

7. An analysis system comprising the sample preprocessing device described in claim 1, and
 an analysis device that analyzes the sample preprocessed by the sample preprocessing device.

8. The sample preprocessing device described in claim 1, wherein a housing space of the housing part conforms to a shape of the sample to keep the sample in the predetermined posture.

9. The sample preprocessing device described in claim 1, wherein the heating furnace and the posture restriction unit are arranged in a housing filled with an inert gas, and the housing part of the posture restriction unit include vents that allow the sample in the housing part to be exposed to inert gas to thereby prevent the sample from being oxidized.

* * * * *